US008864805B2

(12) United States Patent
Deisseroth et al.

(10) Patent No.: US 8,864,805 B2
(45) Date of Patent: **\*Oct. 21, 2014**

(54) SYSTEM FOR OPTICAL STIMULATION OF TARGET CELLS

(71) Applicant: The Board of Trustees of the Leland Stanford Junior University, Palo Alto, CA (US)

(72) Inventors: Karl Deisseroth, Palo Alto, CA (US); Feng Zhang, Cambridge, MA (US); Edward Boyden, Cambridge, MA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/763,119

(22) Filed: Feb. 8, 2013

(65) Prior Publication Data

US 2013/0295635 A1     Nov. 7, 2013

Related U.S. Application Data

(63) Continuation of application No. 12/522,520, filed as application No. PCT/US2008/050745 on Jan. 10, 2008, now Pat. No. 8,398,692.

(60) Provisional application No. 60/879,669, filed on Jan. 10, 2007, provisional application No. 60/903,248, filed on Feb. 23, 2007.

(51) Int. Cl.
*A61N 5/06*      (2006.01)

(52) U.S. Cl.
USPC ......................................................... 607/88

(58) Field of Classification Search
USPC ............. 435/173.1, 289.1, 455, 173.4, 283.1; 604/20; 607/2, 92, 88
See application file for complete search history.

(56) References Cited

U.S. PATENT DOCUMENTS 2,968,302  A    1/1961  Fry et al.
3,131,690  A    5/1964  Innis et al.
(Continued)

FOREIGN PATENT DOCUMENTS

WO    WO2009/119782    10/2009
WO    WO 2010/011404 A3    1/2010
(Continued)

OTHER PUBLICATIONS

Lanyi et al. "The primary structure of a Halorhodopsin from *Natronobacterium pharaonis*" Journal of Biological Chemistry 1990, vol. 265, No. 3, p. 1253-1260.

(Continued)

*Primary Examiner* — Jessica T. Stultz
*Assistant Examiner* — Tuan Nguyen
(74) *Attorney, Agent, or Firm* — Paula A. Borden; Bozicevic, Field & Francis LLP (57) ABSTRACT

Various systems and methods are implemented for controlling stimulus of a cell. One such method is implemented for optical stimulation of a cell expressing a NpHR ion pump. The method includes the step of providing a sequence of stimuli to the cell. Each stimulus increases the probability of depolarization events occurring in the cell. Light is provided to the cell to activate the expressed NpHR ion pump, thereby decreasing the probability of depolarization events occurring in the cell.

10 Claims, 4 Drawing Sheets

(56) References Cited

U.S. PATENT DOCUMENTS

| | | |
|---|---|---|
| 3,499,437 A | 3/1970 | Balamuth et al. |
| 3,567,847 A | 3/1971 | Price |
| 4,343,301 A | 8/1982 | Indech |
| 4,559,951 A | 12/1985 | Dahl et al. |
| 4,616,231 A | 10/1986 | Autrey et al. |
| 4,865,042 A | 9/1989 | Umemura et al. |
| 4,879,284 A | 11/1989 | Land et al. |
| 5,032,123 A | 7/1991 | Katz et al. |
| 5,041,224 A | 8/1991 | Ohyama et al. |
| 5,082,670 A | 1/1992 | Gage et al. |
| 5,249,575 A | 10/1993 | Di Mino et al. |
| 5,267,152 A | 11/1993 | Yang et al. |
| 5,290,280 A | 3/1994 | Daikuzono et al. |
| 5,330,515 A | 7/1994 | Rutecki et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,939,320 A | 8/1999 | Littman et al. |
| 6,134,474 A | 10/2000 | Fischell et al. |
| 6,161,045 A | 12/2000 | Fischell et al. |
| 6,253,109 B1 | 6/2001 | Gielen |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,810,285 B2 | 10/2004 | Pless et al. |
| 6,889,085 B2 | 5/2005 | Dawson |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 8,398,692 B2* | 3/2013 | Deisseroth et al. ............ 607/88 |
| 8,401,609 B2 | 3/2013 | Deisseroth et al. |
| 2002/0094516 A1 | 7/2002 | Calos et al. |
| 2002/0155173 A1 | 10/2002 | Chopp et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0097122 A1 | 5/2003 | Ganz et al. |
| 2003/0104512 A1 | 6/2003 | Freeman et al. |
| 2003/0125719 A1 | 7/2003 | Furnish |
| 2003/0204135 A1 | 10/2003 | Bystritsky |
| 2003/0232339 A1 | 12/2003 | Shu et al. |
| 2004/0034882 A1 | 2/2004 | Vale et al. |
| 2004/0039312 A1 | 2/2004 | Hillstead et al. |
| 2004/0122475 A1 | 6/2004 | Myrick et al. |
| 2004/0203152 A1 | 10/2004 | Calos |
| 2005/0058987 A1 | 3/2005 | Shi et al. |
| 2005/0119315 A1 | 6/2005 | Fedida et al. |
| 2005/0124897 A1 | 6/2005 | Chopra |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0155348 A1 | 7/2006 | deCharms |
| 2006/0161227 A1 | 7/2006 | Walsh et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0031924 A1 | 2/2007 | Li et al. |
| 2007/0053996 A1 | 3/2007 | Boyden et al. |
| 2007/0054319 A1 | 3/2007 | Deisseroth et al. |
| 2007/0060915 A1 | 3/2007 | Kucklick |
| 2007/0135875 A1 | 6/2007 | Demarais et al. |
| 2007/0156180 A1 | 7/2007 | Jaax et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0033569 A1 | 2/2008 | Ferren et al. |
| 2008/0046053 A1 | 2/2008 | Wagner et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1* | 4/2008 | Schneider et al. ......... 424/93.21 |
| 2008/0103551 A1 | 5/2008 | Masoud |
| 2008/0119421 A1 | 5/2008 | Tuszynski et al. |
| 2008/0125836 A1 | 5/2008 | Streeter et al. |

(56) References Cited

U.S. PATENT DOCUMENTS

| | | | |
|---|---|---|---|
| 2008/0167261 | A1 | 7/2008 | Sclimenti |
| 2008/0175819 | A1 | 7/2008 | Kingsman et al. |
| 2008/0200749 | A1 | 8/2008 | Zheng et al. |
| 2008/0221452 | A1 | 9/2008 | Njemanze |
| 2008/0227139 | A1 | 9/2008 | Deisseroth et al. |
| 2008/0228244 | A1 | 9/2008 | Pakhomov et al. |
| 2008/0262411 | A1 | 10/2008 | Dobak |
| 2008/0287821 | A1 | 11/2008 | Jung et al. |
| 2009/0054954 | A1 | 2/2009 | Foley et al. |
| 2009/0069261 | A1 | 3/2009 | Dodge et al. |
| 2009/0088680 | A1 | 4/2009 | Aravanis et al. |
| 2009/0093403 | A1 | 4/2009 | Zhang et al. |
| 2009/0099038 | A1 | 4/2009 | Deisseroth et al. |
| 2009/0112133 | A1 | 4/2009 | Deisseroth et al. |
| 2009/0118800 | A1 | 5/2009 | Deisseroth et al. |
| 2009/0148861 | A1 | 6/2009 | Pegan et al. |
| 2009/0254134 | A1 | 10/2009 | Nikolov et al. |
| 2009/0268511 | A1 | 10/2009 | Birge et al. |
| 2009/0319008 | A1 | 12/2009 | Mayer |
| 2009/0326603 | A1 | 12/2009 | Boggs |
| 2010/0009444 | A1 | 1/2010 | Herlitze et al. |
| 2010/0016783 | A1 | 1/2010 | Bourke et al. |
| 2010/0145418 | A1 | 6/2010 | Zhang et al. |
| 2010/0190229 | A1 | 7/2010 | Deisseroth et al. |
| 2010/0234273 | A1 | 9/2010 | Deisseroth et al. |
| 2011/0092800 | A1 | 4/2011 | Yoo et al. |
| 2011/0105998 | A1 | 5/2011 | Zhang et al. |
| 2011/0112179 | A1 | 5/2011 | Deisseroth et al. |
| 2011/0125077 | A1 | 5/2011 | Denison et al. |
| 2011/0125078 | A1 | 5/2011 | Denison et al. |
| 2011/0159562 | A1 | 6/2011 | Deisseroth et al. |
| 2011/0166632 | A1 | 7/2011 | Deisseroth et al. |
| 2011/0172653 | A1 | 7/2011 | Deisseroth et al. |
| 2011/0301529 | A1 | 12/2011 | Deisseroth et al. |
| 2011/0311489 | A1 | 12/2011 | Deisseroth et al. |
| 2012/0093772 | A1 | 4/2012 | Horsager et al. |
| 2012/0165904 | A1 | 6/2012 | Deisseroth et al. |
| 2012/0253261 | A1 | 10/2012 | Poletto et al. |
| 2013/0019325 | A1 | 1/2013 | Deisseroth et al. |
| 2013/0144359 | A1 | 6/2013 | Kishawi et al. |

FOREIGN PATENT DOCUMENTS

| | | |
|---|---|---|
| WO | WO 2010/056970 | 5/2010 |
| WO | WO 2011/066320 A3 | 6/2011 |
| WO | WO 2011-116238 A2 | 9/2011 |
| WO | WO 2011/127088 A3 | 10/2011 |
| WO | WO 2012/061676 | 5/2012 |
| WO | WO2012/061681 | 5/2012 |
| WO | WO2012/061684 | 5/2012 |
| WO | WO2012/061688 | 5/2012 |
| WO | WO2012/061690 | 5/2012 |
| WO | WO 2012/061744 | 5/2012 |
| WO | WO 2012/134704 A2 | 10/2012 |
| WO | WO 2013/126521 | 8/2013 |
| WO | WO 2013/142196 | 9/2013 |

OTHER PUBLICATIONS

Hofherr et al. "Selective Golgi export of Kir2.1 controls the stoichiometry of functional Kir2.x channel heteromers" Journal of Cell Science, 2005, vol. 118, p. 1935-1943.

Loetterle, et al., "Cerebellar Stimulation: Pacing the Brain", American Journal of Nursing, 1975, vol. 75, No. 6, pp. 958-960.

Takahashi, et al., "Induction of Pluripotent Stem Cells from Mouse Embryonic and Adult Fibroblast Cultures by Defined Factors", 2006, Cell, vol. 126, pp. 663-676.

Tam, B. et al., "Identification of an Outer Segment Targeting Signal in the COOH Terminus of Rhodopsin Using Transgenic *Xenopus laevis*", The Journal of Cell Biology, 2000, vol. 151, No. 7, pp. 1369-1380.

U.S. Appl. No. 13/555,981, filed Jul. 23, 2012, Deisseroth, et al.
U.S. Appl. No. 13/622,809, filed Sep. 19, 2012, Deisseroth, et al.
U.S. Appl. No. 13/623,612, filed Sep. 20, 2012, Deisseroth, et al.
U.S. Appl. No. 13/718,243, filed Dec. 18, 2012, Deisseroth, et al.
U.S. Appl. No. 13/763,132, filed Feb. 8, 2013, Deisseroth, et al.
U.S. Appl. No. 13/772,732, filed Feb. 21, 2013, Deisseroth, et al.
U.S. Appl. No. 13/847,653, filed Mar. 20, 2013, Deisseroth, et al.
U.S. Appl. No. 13/847,785, filed Mar. 20, 2013, Deisseroth, et al.
U.S. Appl. No. 13/849,913, filed Mar. 25, 2013, Deisseroth, et al.
U.S. Appl. No. 13/850,426, filed Mar. 26, 2013, Deisseroth, et al.
U.S. Appl. No. 13/850,428, filed Mar. 26, 2013, Deisseroth, et al.
U.S. Appl. No. 13/850,436, filed Mar. 26, 2013, Deisseroth, et al.
U.S. Appl. No. 13/850,709, filed Mar. 26, 2013, Deisseroth, et al.
U.S. Appl. No. 13/854,750, filed Apr. 1, 2013, Deisseroth, et al.
U.S. Appl. No. 13/854,754, filed Apr. 1, 2013, Deisseroth, et al.
U.S. Appl. No. 13/855,413, filed Apr. 2, 2013, Deisseroth, et al.
U.S. Appl. No. 13/875,966, filed May 2, 2013, Deisseroth, et al.
U.S. Appl. No. 13/882,566, filed Nov. 4, 2011, Deisseroth, et al.
U.S. Appl. No. 13/882,666, filed Nov. 4, 2011, Deisseroth, et al.
U.S. Appl. No. 13/882,670, filed Nov. 4, 2011, Deisseroth, et al.
U.S. Appl. No. 13/882,703, filed Nov. 4, 2011, Deisseroth, et al.
U.S. Appl. No. 13/882,705, filed Nov. 4, 2011, Deisseroth, et al.
U.S. Appl. No. 13/882,719, filed Nov. 4, 2011, Deisseroth, et al.

Tye, et al. "Optogenetic investigation of neural circuits underlying brain disease in animal models," Nature Reviews Neuroscience (Mar. 2012), 13(4):251-266.

Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.

Han, et al., "Multiple-Color Optical Activation, Silencing, and Desynchronization of Neural Activity with Single-Spike Temporal Resolution", PLoS One, 2007, vol. 2, No. 3, pp. 1-12.

Kinoshita, et al., "Optogenetically Induced Supression of Neural Activity in the Macaque Motor Cortex", Poster Sessions Somatomotor System, Others,2010, pp. 141-154.

Rein, et al., "The Optogenetic (r)evolution", Mol. Genet. Genomics, 2012, vol. 287, No. 2, pp. 95-109.

Remy, et al., "Depression in Parkinson's Disease: Loss of Dopamine and Noradrenaline Innervation in the Limbic System", Brain, 2005, vol. 128 (Pt 6), pp. 1314-1322.

Tsai, et al., "Phasic Firing in Dopaminergic Neurons in Sufficient for Behavioral Conditioning", Science, 2009, vol. 324, pp. 1080-1084.

Zhao, et al., "Improved Expression of Halorhodopsin for Light-Induced Silencing of Neuronal Activity", Brain Cell Biology, 2008, vol. 36 (1-4), pp. 141-154.

Gradinaru, et al., Molecular and Cellular Approaches for Diversifying and Extending Optogenetics, Cell, 2010, vol. 141, No. 1, pp. 154-165.

RecName: Full=Halorhodopsin; Short=HR; Alt Name: Full=NpHR; XP002704922, retrieved from EBI accession No. UNIPROT: P15647. Database accession No. P15647. Apr. 1, 1990.

"N. pharaonis halorhodopsin (hop) gene, complete cds.", XP002704883, retrieved from EBI accession No. EMBL: J05199. Database accession No. J05199. Nov. 22, 1990.

"Subname: Fluu=Bacteriorhodopsin"; XP002704863, retrieved from EBI accession No. UNIPROT: B0R5N9. Database accession No. B0R5N9. Apr. 8, 2008.

Zhang, et al., "The Microbial Opsin Family of Optogenetic Tools", Cell, 2011, vol. 147, No. 7, pp. 1146-1457.

Balint, et al., "The Nitrate Transporting Photochemical Reaction Cycle of the Pharaonis Halorhodopsin", Biophysical Journal, 2004, vol. 86, pp. 1655-1663.

Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.

Xiong et al., "Interregional connectivity to primary motor cortex revealed using MRI resting state images", Hum Brain Mapp, 1999, 8(2-3):151-156.

Arenkiel, et al. "In vivo light-induced activation of neural circuitry in transgenic mice expressing Channelrhodopsin-2", Neuron, 2007, 54:205-218.

Milella et al. "Opposite roles of dopamine and orexin in quinpirole-induced excessive drinking: a rat model of psychotic polydipsia" Psychopharmacology, 2010, 211:355-366.

Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.

* cited by examiner

SYSTEM FOR OPTICAL STIMULATION OF TARGET CELLS

RELATED PATENT DOCUMENTS

This patent document claims benefit under 35 U.S.C. §119(e) both of U.S. Provisional Application No. 60/879,669 filed on Jan. 10, 2007 and entitled "Genetically-Targetable Optical Inactivation of Excitable Cells" and of U.S. Provisional Application No. 60/903,248 filed on Feb. 23, 2007 and entitled "Genetically-Targetable Optical Inactivation of Excitable Cells," each of which are fully incorporated by reference.

FIELD OF THE INVENTION

The present invention relates generally to systems and approaches for stimulating target cells, and more particularly, to using optics to dissuade stimulation-generated pulse trains.

BACKGROUND

Various efforts in neuroscience are directed towards determining whether neural activity in a specific brain region, or in a set of genetically-identified neurons, contributes to a particular neural computation, behavior, or neurological or psychiatric disorder. For centuries, insights have come from studies of human patients with specific lesions, as exemplified by Paul Broca's delineation in the 1860s of the eponymous brain area that, when dysfunctional, results in deficits of speech production. Many studies have used ablation or pharmacological shutdown of neurons or brain regions in animals, or careful analysis of patients, to parse out the physical substrates of normal and abnormal behavior. However, growing awareness that activity in multiple brain regions may be coordinated during performance of a behavior, or in a particular neural dysfunction, has raised the question of precisely when specific brain regions or neurons contribute. For example, a large number of in vivo recording studies have demonstrated, for many brain regions, that specific neurons can fire action potentials during precise intervals within a behavioral task. The intervals can last as little as a fraction of a second; it is possible that specific brain regions or neurons are required only at specific times in a task, not continuously. In humans, use of transcranial magnetic stimulation to disrupt the visual cortex has demonstrated that conscious perception requires intact cortical performance during temporal windows that last tens of milliseconds, occurring at precise times after visual stimulus presentation. Accordingly, a method for disrupting activity in targeted cell types for very precisely delimited periods of time (e.g., several milliseconds) could help answer a number of outstanding questions, and enable novel ones to be asked. For example, one question involves the identification of the precise brain regions, cell types, and activity patterns required at each phase (sensory, decision-making and motor) of a behavioral task. Another question involves, for a particular perception (e.g., feeling, decision, memory, or action) identifying the precise number of neurons that must be active within a certain region and how long the neurons are active. Another question involves the identification of the causal role of neural synchrony and precise spike timing in neural computation, plasticity, and pathological brain function. As memories are encoded, consolidated, and forgotten, it can be important to identifying how the critical neural loci of memory changes.

SUMMARY

The claimed invention is directed to photosensitive biomolecular structures and related methods. The present invention is exemplified in a number of implementations and applications, some of which are summarized below.

According to one example embodiment of the present invention, a method is implemented for optical stimulation of a cell expressing an NpHR ion pump. The method includes the step of providing a sequence of stimuli to the cell. Each stimulus increases the probability of depolarization events occurring in the cell. Light is provided to the cell to activate the expressed NpHR ion pump, thereby decreasing the probability of depolarization events occurring in the cell.

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for enabling practical application of a variety of photosensitive bio-molecular structures, and the invention has been found to be particularly suited for use in arrangements and methods dealing with neuron stimulation. While the present invention is not necessarily limited to such applications, various aspects of the invention may be appreciated through a discussion of various examples using this context.

The aspects of the present invention are directed to a technology that enables rapid neural inactivation and release from inactivation at the millisecond timescale, is safe and effective, has minimal effects on cellular physiology or survival, and requires no exogenous chemicals to be delivered. A specific embodiment of the invention involves a single-component protein capable of mediating light-induced inhibition, the mammalian codon-optimized version of the light-driven chloride pump halorhodopsin, from the archaebacterium *Natronobacterium pharaonis* (abbreviated Halo). Although such halobacteria are known to live in very high saline concentrations (e.g., >1 M), some wild-type halorhodopsins have been shown to preserve functionality at much lower chloride concentrations, even at levels comparable to those found in mammalian cerebrospinal fluid. Applications of the present invention involve the use of Halo to mediate optical inhibition of neuronal spiking in a physiologically accurate milieu, in response to pulses of somatically injected intracellular current (~300 PA), with temporal onset and offset of inhibition in the range of 10-15 milliseconds. Moreover, Halo can mediate naturalistic trains of inhibitory voltage changes at physiologically relevant frequencies, with minimal attenuation of voltage amplitude from pulse to pulse.

Aspects of an embodiment of the invention are also directed to a single neuron expressing both Halo and the blue-light driven cation channel Channelrhodopsin-2 (ChR2), neural inhibition and excitation are controlled at the millisecond timescale by pulses of yellow and blue light, respectively. In one instance, these channels provide the capability to create lesions of virally or transgenically targeted neural circuits over precise timescales, as well as neuroengineering interfaces for bi-directional control of excitable cell depolarization and hyperpolarization.

One embodiment of the present invention involves a designed fusion protein having the mammalian codon-optimized form of *N. pharaonis* halorhodopsin (Halo), with EGFP added in-frame at the C-terminus for ease of visualization. When expressed using the CaMKII promoter, which targets excitatory neurons of the forebrain, Halo-EGFP fluoresced brightly and appeared evenly distributed in the neuron. When exposed to ~10 m W/mm$^2$ yellow light (e.g., from a xenon lamp, filtered by a standard Texas red excitation filter (bandpass, 560±27.5 nm, Chroma), voltage-clamped hippocampal neurons expressing Halo can experience outward currents with rapid onset, stable steady-state, and abrupt shut-off with cessation of illumination. In some instances, no supplementation of the culture medium or the recording medium with the halorhodopsin cofactor all-trans retinal is necessary. This is believed to be due to levels of all-trans retinal naturally occurring in mammalian neurons in culture and in live brain that are high enough to enable type I opsins without chemical supplementation.

Figure 1:
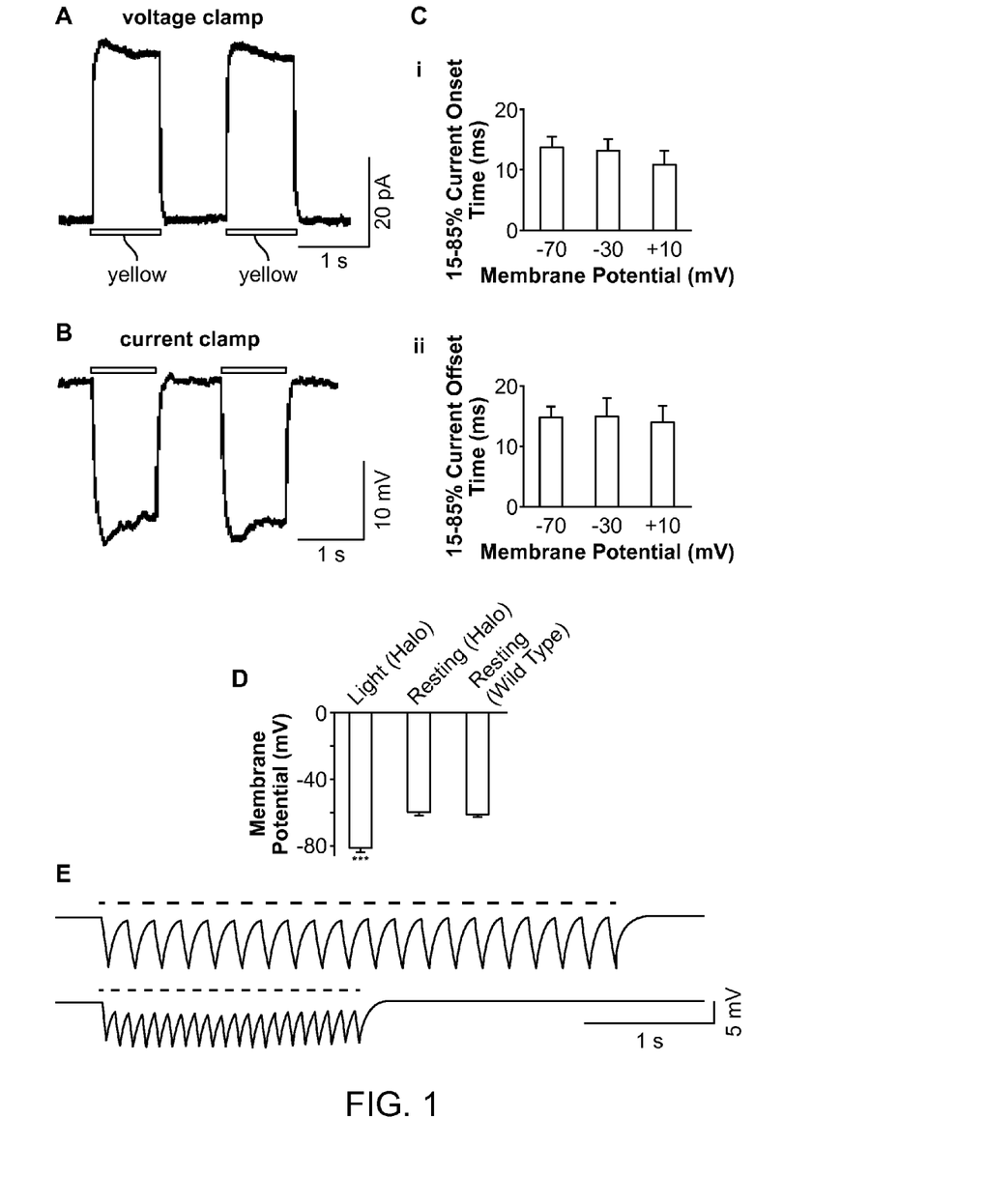
FIG. 1A shows sample outward currents elicited by two pulses of yellow light in a voltage-clamped neuron, consistent with an embodiment of the present invention.
FIG. 1B shows sample membrane voltage hyperpolarizations elicited by two pulses of yellow light, in a current-clamped neuron held at resting membrane potential, consistent with an embodiment of the present invention.
FIG. 1C shows Kinetic properties of yellow light-elicited, Halo-mediated currents from voltage-clamped neurons, consistent with an embodiment of the present invention.
FIG. 1D shows membrane potentials of neurons expressing Halo-GFP and exposed to yellow light, neurons expressing Halo-GFP but not exposed to any light, and neurons without transfection with Halo-GFP, consistent with an embodiment of the present invention.
FIG. 1E shows sample membrane hyperpolarizations induced by 5 Hz and 10 Hz trains of yellow light pulses, consistent with an embodiment of the present invention.

FIG. 1 shows the results of an experimental test of millisecond-timescale, yellow light-driven, neuronal hyperpolarization with Halo. A cultured hippocampal neuron expressing mammalian codon-optimized *N. pharaonis* halorhodopsin (Halo) fused to GFP under the CaMKII promoter is used.

FIG. 1A shows sample outward currents elicited by two 1-second pulses of yellow (560±27.5 nm) light (~10 mW/mm$^2$) in a voltage-clamped neuron held at −70 mV. Yellow bars in this and subsequent figures indicate the period of yellow light exposure.

FIG. 1C shows Kinetic properties of yellow light-elicited, Halo-mediated currents from voltage-clamped neurons. FIG. 1Ci shows 15-85% current onset time. FIG. 1Cii shows 85-15% offset time. For each measurement, data is presented from neurons held at −70 mV (n=14 neurons), −30 mV (n=10), and +10 mV (n=10) (left to right). Bars represent mean±standard error of the mean (S.E.M.).

FIG. 1B shows sample membrane voltage hyperpolarizations elicited by two 1-second pulses of yellow light, in a current-clamped neuron held at resting membrane potential.

FIG. 1D shows membrane potentials of neurons expressing Halo-GFP and exposed to yellow light (left, n=14), expressing Halo-GFP but not exposed to any light (middle, n=11), and without transfection with Halo-GFP (right, n=8). *** denotes significant difference between the Halo-GFP+light condition and each of the other two conditions (p<0.0001; Fisher's partial least-squares difference (PLSD) post hoc test after ANOVA).

FIG. 1E shows sample membrane hyperpolarizations induced by 5 Hz (top) and 10 Hz (bottom) trains of yellow light pulses, with light pulse durations of 50 ms (top) and 25 ms (bottom), respectively.

In related experimental tests, the light pulses elicited pulse amplitudes of 56.9±23.4 pA (mean±st. dev.; n=14 neurons). Repeating a 1-second pulse of yellow light twice, spaced by 1 second in darkness, resulted in identical pulse amplitudes each time (p>0.50, paired t-test), as shown in FIG. 1A.

This stable current amplitude appears to be consistent with what is known about the halorhodopsin photocycle. As befits a chloride pump, the current amplitude did not vary significantly with holding voltage (F=0.004, p>0.95, ANOVA with factor of holding voltage), nor did any measured kinetic parameters vary, such as the onset or offset times of the current pulses (F<0.6, p>0.55 for all comparisons, ANOVA; FIG. 1C). The onset and offset times of elicited currents were seen to be on the order ~10-15 ms at all holding voltages tested. This suggests that Halo is a viable candidate for ultratransient shutdown of spike trains (FIG. 1Ci, 1Cii). When held in current clamp, hippocampal neurons underwent peak hyperpolarizations of −21.6±11.3 mV (mean±st. dev.; n=11 neurons) in response to pulses of yellow light, with no difference between the peak hyperpolarizations achieved by two pulses separated by a 1-second pause (p>0.85, paired t-test; FIG. 1B). These large voltage changes were relatively rapid, with onset and offset times of 68±57 and 73±39 ms, respectively. Thus, Halo has been shown to be capable of reliably mediating hyperpolarizations of significant magnitude, with fast onset and offset times at the beginning and end of light exposure.

Several control experiments were implemented to evaluate whether Halo has unanticipated side effects, such as altering basal cell physiology or increasing the propensity for cell death. First, the basal state of Halo-expressing neurons electrophysiologically was characterized when no light was present. When measured in darkness, no difference was seen between the resting potentials of neurons expressing Halo and those of neighboring neurons in the culture that were untransfected (p>0.20, n=11 Halo-positive cells, n=8 Halo-negative cells; FIG. 1D). This result suggests that basal neural activity would be little affected by the presence of Halo. On the other hand, Halo-expressing neurons illuminated with yellow light were significantly hyperpolarized, with respect to both Halo-expressing neurons in darkness and non-transfected cells (p<0.0001 for both of these comparisons, Fisher's partial least squares difference post hoc test after ANOVA (F=28.4, p<0.0001) with factor of experimental condition; FIG. 1D). An independent assay for unanticipated effects on cell health, the membrane-impermeant DNA stain ethidium homodimer-1 was used to detect the cell membrane breakdown accompanying cell death for one week in Halo-expressing cells. Little difference was found in the prevalence of cell death between Halo-positive and Halo-negative neurons: 16/308 (5.2%) non-transfected neurons counted, and 1/22 (4.5%) Halo-expressing neurons counted, were labeled by ethidium homodimer-1, indicating that Halo was not toxic over the course of the one-week experiment ($x2=0.02$, p>0.85).

In an effort to explore the uses Halo could present in the analysis and engineering of intact neural circuits, an experiment was performed to determine whether the fast response times of Halo could support naturalistic sequences of hyperpolarization events, in response to trains of brief pulses of yellow light.

Figure 2:
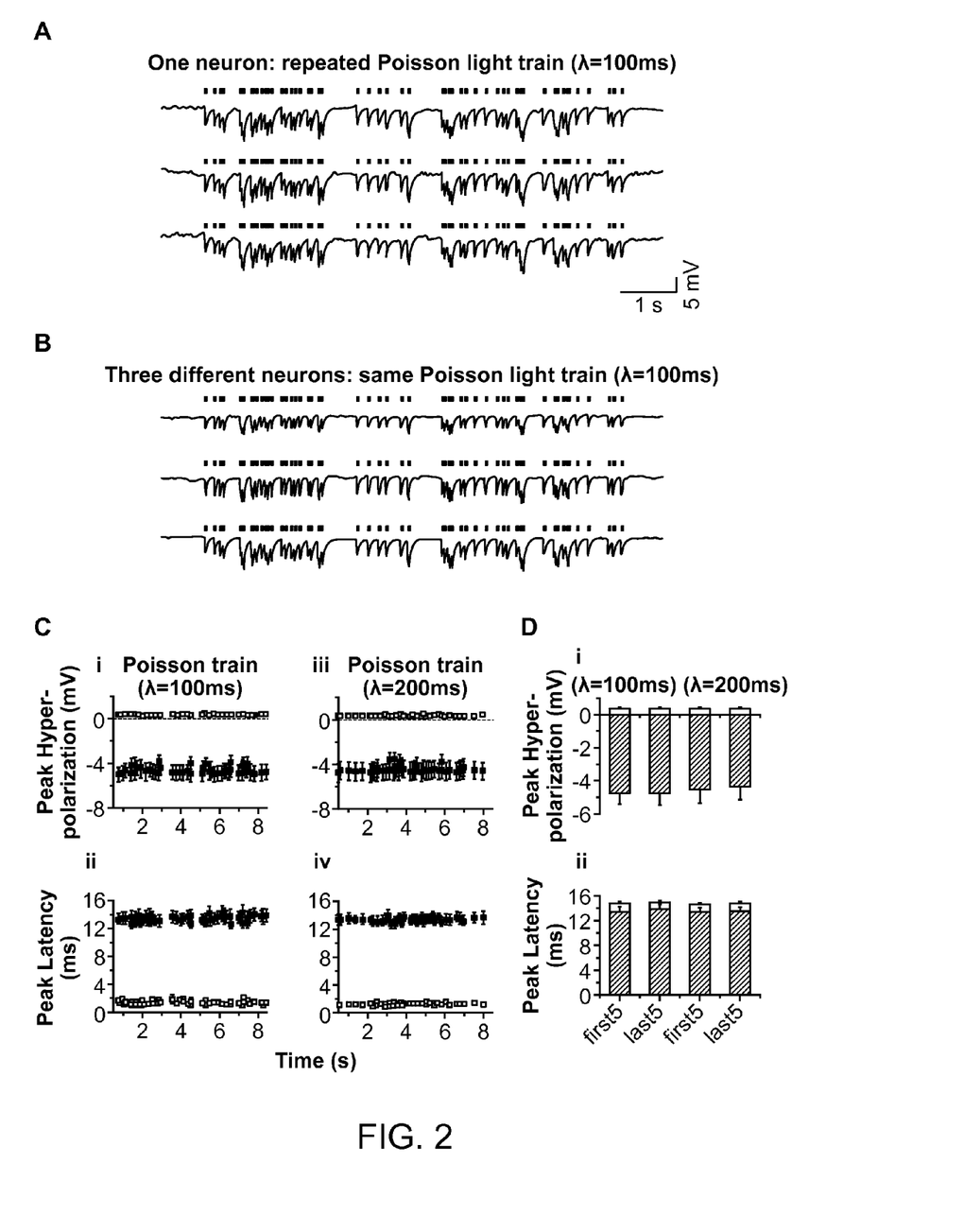
FIG. 2A shows three voltage traces of a current-clamped hippocampal neuron, exposed to a Poisson train of yellow light pulses, consistent with an embodiment of the present invention.
FIG. 2B shows voltage traces of three different current-clamped neurons exposed to the same Poisson train of light pulses ($\lambda$=100 ms), consistent with an embodiment of the present invention.
FIG. 2C shows properties of hyperpolarization events elicited by Poisson trains with various inter-pulse intervals, consistent with an embodiment of the present invention.
FIG. 2D shows a comparison of the peak hyperpolarization and the time-to-peak data at the beginning and end of the Poisson trains, for the neurons described in FIG. 2C, consistent with an embodiment of the present invention.

FIG. 2 shows high-fidelity Halo-mediated naturalistic trains of inhibitory events. FIG. 2A shows three voltage traces of a current-clamped hippocampal neuron, exposed to a Poisson train of yellow light pulses. Each light pulse lasts 10 ms, and the Poisson train has a mean inter-pulse interval of $\lambda=100$ ms.

FIG. 2B shows voltage traces of three different current-clamped neurons exposed to the same Poisson train of light pulses ($\lambda=100$ ms).

FIG. 2C shows properties of hyperpolarization events elicited by Poisson trains with inter-pulse interval $\lambda=100$ ms (i, ii) and $\lambda=200$ ms (iii, iv), plotted versus onset time of each light pulse. Plots (i) and (iii) show the peak of each hyperpolarization event, as well as the across-trials standard deviation of these amplitude values across ten trials. Plots (ii) and (iv) show the latency between the onset time of the light pulse and the time of the hyperpolarization peak, as well as the across-trials standard deviation of these timing values across ten trials. All plotted points are across-neuron mean±S.E.M. (n=5 neurons).

FIG. 2D shows a comparison of the peak hyperpolarization (i) and the time-to-peak (ii) data at the beginning (first 5) and end (last 5) of the $\lambda=100$ ms and $\lambda=200$ ms Poisson trains, for the n=5 neurons described in FIG. 2C. In (i): for each neuron, the average of the first 5 or last 5 hyperpolarization peaks or the across-trials standard deviation of these amplitude values was first computed, then the across-neuron mean±S.E.M. was plotted. In (ii): for each neuron, the average of the first 5 or last 5 times-to-peak or the across-trials standard deviation of these times-to-peak were first computed, then the across-neuron mean±S.E.M. was plotted.

FIG. 2A shows three traces of hyperpolarization events elicited in a single neuron, resulting from repeatedly playing back a Poisson train (mean inter-pulse interval, $\lambda=100$ ms, 59 pulses), of 10 ms-duration yellow light pulses, to simulate stochastic synaptic inhibitory input. FIG. 2B shows three such hyperpolarization traces, taken from different neurons. The variability of such trains was remarkably low in many regards—across ten repeated trials in a single cell, across multiple cells (n=5 neurons), and over time throughout a sustained train of 59 pulses (FIGS. 2C, 2D). It was found that for hyperpolarizations elicited by 10 ms-duration light pulses during a $\lambda=100$ ms Poisson train, the mean amplitude was −4.56 mV (averaged across trials and neurons), but the trial-to-trial standard deviation of this amplitude was only 0.40 mV (averaged across neurons, FIG. 2Ci and FIG. 2Di). The trial-to-trial jitter of the time the hyperpolarization took to reach its peak value was also small, 1.27 ms (averaged across neurons, FIG. 2Cii and FIG. 2D ii). The neuron-to-neuron variability of amplitude and timing was somewhat larger than the trial-to-trial variability, with standard deviations of 1.45 mV and 1.78 ms, respectively, but demonstrating that precise inhibitory control of a population of neurons could proceed with millivolt and millisecond resolution. Finally, the through-train sustainability of light-elicited voltage changes was quantitatively examined by comparing the amplitude mean and amplitude variability, and timing variability of the hyperpolarization events elicited by the first five light pulses to those of the last five light pulses in the train (FIGS. 2Di and 2Dii, left side). Little or no difference was seen for any of these statistics between the beginning and end of a train (p>0.10 for all measures, t-test). Identical conclusions held for the $\lambda=200$ ms Poisson train with 46 pulses (FIGS. 2Ciii and 2Civ, and FIGS. 2Di and 2Dii, right side). The high temporal and amplitude fidelity of Halo-mediated hyperpolarizations suggests uses for Halo in simulating inhibitory synaptic inputs, with great precision.

Figure 3:
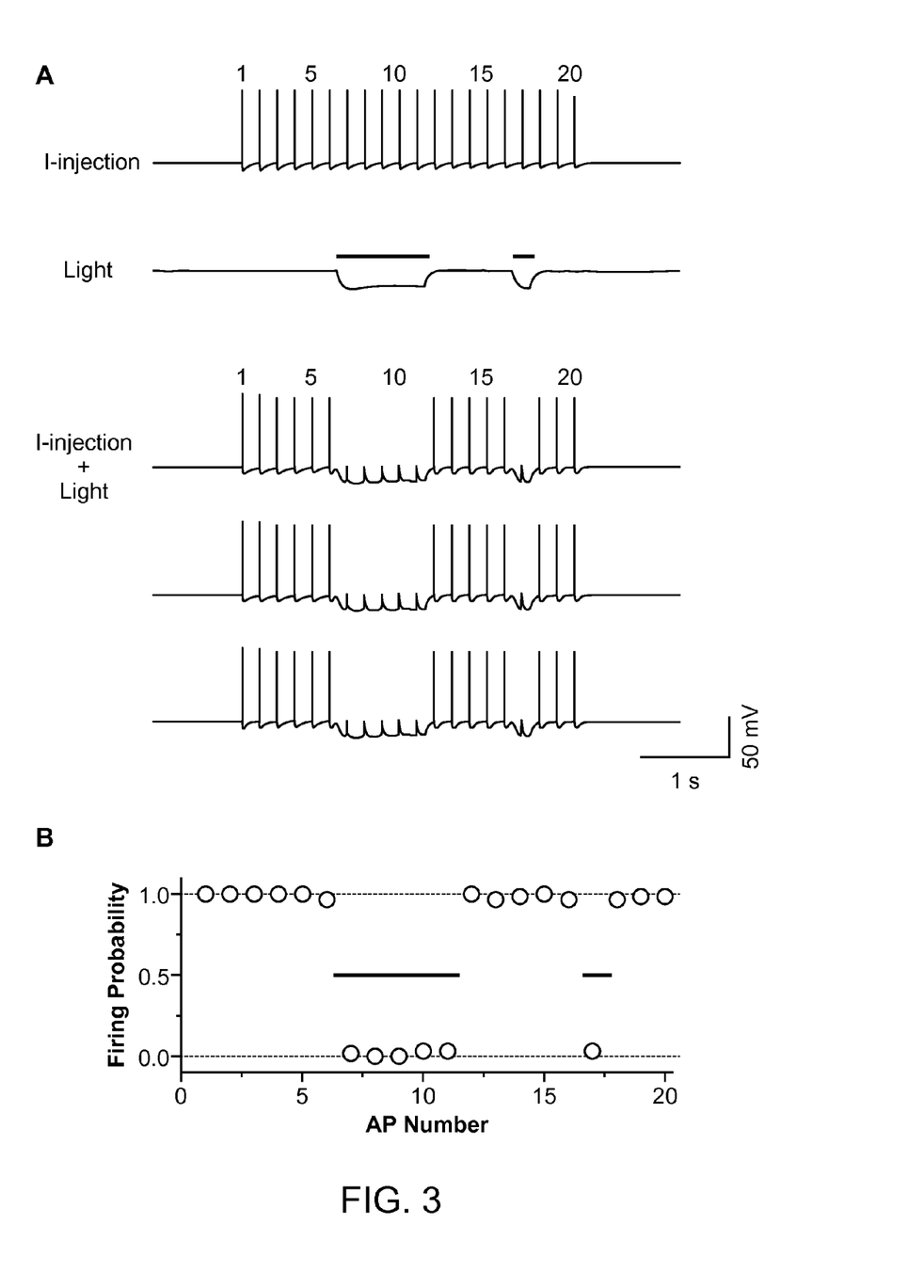
FIG. 3A shows a light-driven spike blockade, demonstrated for a single hippocampal neuron, consistent with an embodiment of the present invention.
FIG. 3B shows population data (n=6 neurons) for light-driven, Halo-mediated spike blockade, consistent with an embodiment of the present invention.

FIG. 3 shows reliable and repeatable Halo-mediated neural inactivation, at single-spike temporal resolution. FIG. 3A shows a light-driven spike blockade, demonstrated for a single hippocampal neuron. At the top of FIG. 3A, labeled with "I-injection," neuronal firing of 20 spikes at 5 Hz are induced by pulsed somatic current injection (~300 pA, 4 ms). In the middle of FIG. 3A, labeled with "light," light membrane hyperpolarizations are induced by two periods of yellow light, timed so as to be capable of blocking spikes 7-11 and spike 17 out of the train of 20 spikes. At the bottom of FIG. 3A, labeled as "I-injection+Light", yellow light drives Halo to block neuron spiking (note significant reductions of spikes 7-11 and of spike 17), while leaving spikes elicited during periods of darkness largely intact.

FIG. 3B shows population data (n=6 neurons) for light-driven, Halo-mediated spike blockade, showing high spike probability during periods of darkness (spikes 1-6, 12-16, and 18-20), and low spike probability during periods of yellow-light illumination (spikes 7-11 and spike 17). Error bars are smaller than the points plotted.

Such experiment were implemented to analyze the ability of Halo to enable rapidly inducible and reversible silencing of neuron spiking. Such ability can be useful to enable time-resolved parsing of the precise neural substrates of behavior. Neurons were intracellularly injected with trains of somatic current pulses (~300 PA, lasting ~4 ms), causing them to fire action potentials at 5 Hz with 100% success rate (FIG. 3A, "I-injection"). Yellow-light pulses were scheduled to occur during the times when certain spikes (i.e., spikes 7-11 and 17) would occur during the somatic current injection protocol (FIG. 3A). The light pulses and the somatic current pulses were presented together (FIG. 3A, "I-injection+light", three trials shown). Spiking was effectively blocked during the periods of yellow-light exposure. The rapid onset and offset kinetics of Halo allowed the deletion of even single spikes.

For instance, the second yellow-light pulse, timed for silencing just spike 17, was able to effectively eliminate spike 17 without affecting the firing of spikes 16 or 18 at all. The experiment was repeated five times on each of n=6 neurons (FIG. 3B). During periods when the yellow light was off, it was found that somatic current pulses elicited a spike 98.7% of the time. In contrast, during periods when the yellow light was on, somatic current pulses elicited a spike only 1.2% of the time. The second pulse of yellow light reduced the probability of firing spike 17 to 3.3%, whereas spikes 16 and 18 still fired 96.7% of the time, not significantly different from the spikes at the beginning of the train, before any light exposure at all ($X^2$=1.02, p>0.30). The temporal precision of Halo in silencing spikes therefore offers the possibility of creating ultratransient (yet precise and effective) lesions of activity in targeted neurons.

A specific embodiment of the present invention includes the use of one member of the type I opsin family, Channelrhodopsin-2 (ChR2), which has received recent attention for its ability to drive neural excitation in response to pulses of blue light (centered around 470 nm). The ability to drive excitation and inhibition in the same neuron, using two different wavelengths of light, could enable answers to questions for which no current technology peinlits resolution. For example, synchronous neural activity has been correlated with higher-order functions, such as attention and abnormal patterns of neural synchrony that are associated with certain neurological and psychiatric disorders. The ability to drive a neuron with balanced but randomly varying excitation and inhibition may allow alteration of the precise timing of membrane voltage fluctuations, in principle permitting neural synchronization or desynchronization without any side effects, such as alteration of spike rate. This may open up new experiments in testing the causal role of neural synchrony in behavior and pathology.

Figure 4A:
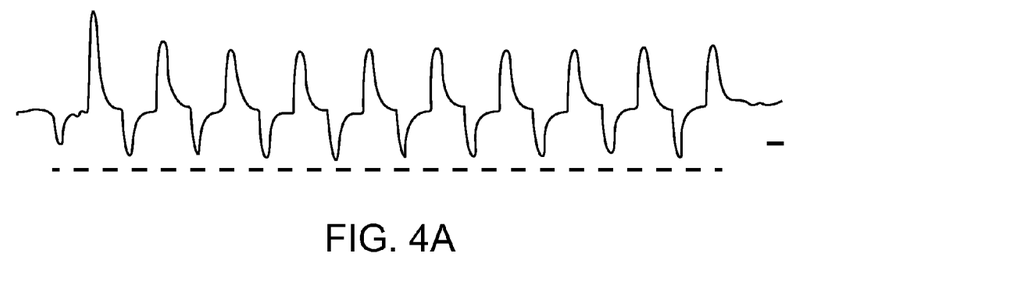
FIG. 4A shows responses of single neurons co-expressing Halo and ChR2, both under control of the CaMKII promoter, to rapidly-switched pulses of yellow and blue light, consistent with an embodiment of the present invention.
Figure 4B:
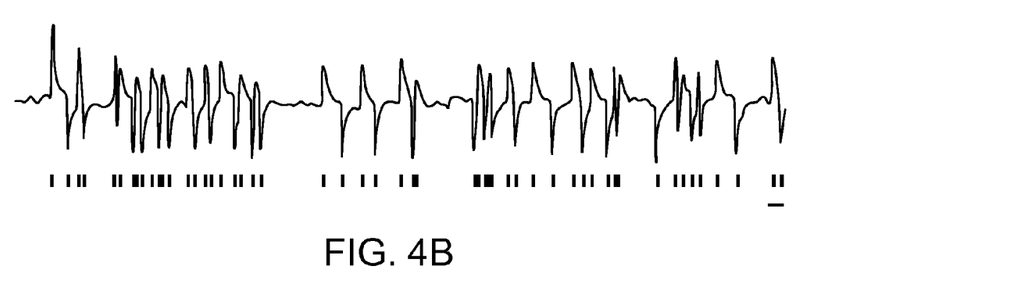
FIGS. 4B-4D show poisson trains of rapidly-alternating yellow and blue light pulses elicited rapidly-alternating hyperpolarizations and depolarizations in the same neuron, consistent with an embodiment of the present invention.
Figure 4C:
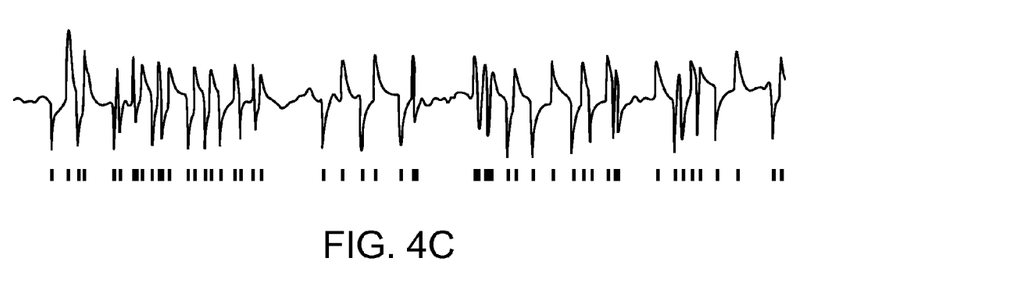
Figure 4D:
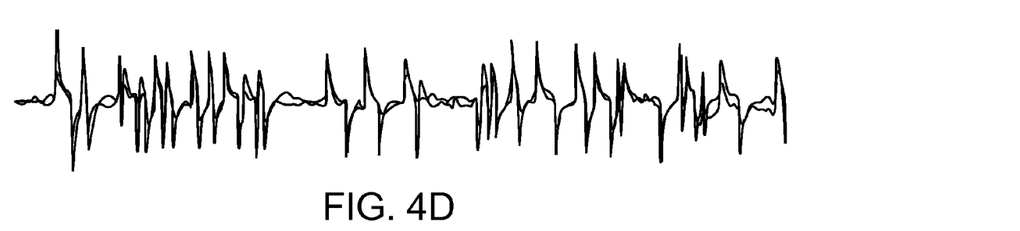

Single neurons co-expressing Halo and ChR2, both under control of the CaMKII promoter, were implemented to allow for response to rapidly-switched pulses of yellow and blue light with hyperpolarizations and depolarizations, respectively (FIG. 4A). Poisson trains ($\lambda$=100 ms) of rapidly-alternating yellow and blue light pulses elicited rapidly-alternating hyperpolarizations and depolarizations in the same neuron (FIG. 4B). In one experiment, the same Poisson train was played back twice with the first train beginning on a blue pulse FIG. 4B and the second train beginning on a yellow pulse, FIG. 4C so that in the second trace, depolarizations were converted into hyperpolarizations and vice versa. In principle, these traces should be quite similar, but with inverted voltage scale. Indeed, FIG. 4C shows an inverted trace superimposed over the trace in FIG. 4B. The degree of superposition suggests that this approach may indeed be a viable method for high-fidelity, bi-directional control of neural activity at the millisecond timescale (FIG. 4C).

The inhibition provided by Halo is strong enough to silence neurons firing spikes in response to significant intracellular somatic current injections (FIG. 3), yet the photocurrents can appear and disappear within 10-15 milliseconds of light onset and offset, respectively (FIG. 1). Furthermore, the amplitude and timing of responses is reliable from trial to trial, and the amplitude of the voltage changes induced by pulses of yellow light does not detectably run down over time (FIG. 2). The use of Halo can be particularly useful for a number of reasons. For example, the timescale of inducing of and subsequent release of voltage inhibition by Halo is relatively fast.

According to another embodiment of the present invention, Halo is used without ChR2. Millisecond pulses of light can be used with Halo-expressing cells to induce hyperpolarizations of several millivolts, and therefore, may be useful for simulating background or well-timed synaptic activity. Studying the function of not only specific cell types, but specific classes of inhibitory synapse, can be accomplished by creating fusion proteins in which Halo is targeted to specific locations where inhibitory synapses uniquely cluster, such as the axon initial segment.

The ability to functionally lesion brain regions or cell types in a rapidly reversible fashion opens up a large class of experiments in which specific neuron populations must be inactivated for precise, sub-second durations during a task. ChR2, another type I opsin which obligately requires all-trans-retinal for its function, has been shown to function in slices of mammalian brain tissue, or even in the central nervous system in vivo, without needing any chemical supplementation. Therefore, it is believed that no supplementation will be needed for Halo in the intact mammalian brain and in brain slice experiments. Other labs working on classical neural model organisms such as *Drosophila* and *C. elegans* have devised ways of delivering all-trans-retinal to the nervous systems of such animals in order to enable ChR2 function, and thus, it is likely that these retinal-delivery protocols would also work for enabling Halo function in these invertebrates.

The ability to study the causal role of neural synchrony in behavior, neural computation, and neural pathology may be a particularly significant role for ChR2 and Halo, working in concert. The newly-enabled power to drive both excitation and inhibition of genetically-targeted neurons with blue and yellow light seems to be particularly valuable for probing synchrony by utilizing multiple wavelengths to perform both excitation and inhibition in the same specimen. The ability to synchronize and desynchronize neurons by balanced, yet random, patterns of excitation and inhibition may open up new horizons into understanding the causal role of neural synchrony in brain function and disease, an area of longstanding, yet growing, interest.

Optical methods for altering neural circuit function have appeal in part because in principle they can use technology developed for brain imaging. The ability to use optical fibers to image deep neural circuits, for example, also enables the stimulation of deep brain structures. Two-photon excitation methods may prove valuable for driving opsin activities, up to 1 mm deep. Another key aspect of optical methods of neural control is the speed with which activation and inactivation can take place, since it is trivial to modulate light intensity at high speeds, faster than most physiologically relevant processes. Nevertheless, non-optical and chemical approaches will continue to find many powerful uses for reliable, enduring inhibition of specific brain circuits and cell types, especially when large regions of deep brain tissue are involved.

From a neuroengineering standpoint, optical prosthetics capable of inhibiting neural activity may present less-invasive strategies for treating disorders of neural hyperactivity. ChR2 has already proven to be well-tolerated in intact mammalian neural circuits for up to a year. If Halo gains a similar track record, it is possible that Halo-enabled prosthetics may open up new horizons in controlling disorders of excitable cells, such as epilepsy, depression, neuropathic pain, and cardiac hyperexcitability. In the immediate future, the ability to study the effects of well-timed neuron or circuit inactivation in animal models of disease will rapidly reveal new principles for selecting neural circuit targets for treatment of specific disorders. There are also implications of the use of Halo in biotechnological scenarios, such as high-throughput drug screening. Several proposals (and even commercially-available systems) exist for using electrical stimulation to activate excitable cells, thus facilitating the screening of depolarization-gated ion channels. The discovery of drugs that target hyperpolarization-activated channels, such as the family of channels mediating the hyperpolarization-activated cation currents I(h) and I(f), may be useful for identifying possible drugs for tackling problems such as absence seizures, bradycardia, and other disorders. An all-optical method for screening for such drugs, which uses light of one frequency to drive inhibition, and light of another frequency to observe changes in fluorescence of an ion-sensitive chemical or genetically encoded sensor, may revolutionize this process. Thus, Halo not only presents a number of unique features that enable effective, and rapidly inducible and reversible, inhibition to be applied to a number of neural circuit questions, but may open up new horizons in biotechnology as well.

An experimental hippocampal neuron culture, transfection, and survival assay was implemented according to the following methods. Hippocampal regions CA3-CAI of postnatal day 0 or day 1 Sprague-Dawley rats (Charles River) were isolated and treated with trypsin (1 mg/ml) for 12 minutes. Digestion was stopped by Hanks solution supplemented with 20% fetal bovine serum and trypsin inhibitor. Tissue was dissociated with silicone-coated Pasteur pipettes and centrifuged at 1000 rpm at 4° C. for 10 minutes. Dissociated neurons were plated on glass coverslips pre-coated with Matrigel (BD Biosciences) at a rough density of approximately two hippocampi per 24 coverslips. Neurons were transfected using a commercially available calcium phosphate transfection kit (Invitrogen), at 3-5 days in vitro. GFP fluorescence was used to identify successfully-transfected neurons, indicating a net transfection efficiency of ~7%. All images and electrophysiological recordings were made on 9-15 day-in-vitro neurons (approximately 4-10 days after transfection). Confocal images of transfected neurons were taken with a Zeiss LSM 510 confocal microscope. Cell death count was carried out on living cultures, seven days after transfection, by adding 4 µM ethidium homodimer-1 (Invitrogen) to the culture medium for 10 minutes at 37° C., then washing the cells with Tyrode's solution (see below). GFP-positive and negative neurons were counted for positive and negative ethidium fluorescence, in five regions on each of three coverslips for this viability assay.

An experiment regarding electrophysiology and optical methods was implemented according to the following methods. Whole cell patch clamp recording was made on 9-15 day-in-vitro neurons using a Multiclamp 700B amplifier, connected to a Digidata 1440 digitizer (Molecular Devices) attached to a PC running pClamp 10. During recording, neurons were bathed in Tyrode's solution containing (in mM) 138 NaCl, 2.4 KCl, 2 CaCl, 2 MgCl, 10 HEPES, 10 Glucose, 24 sucrose, 10 µM NBQX, 10 µM gabazine and 50 µM D-APV. Borosilicate glass (Warner) pipettes were filled with a solution containing (in mM) 130 K-Gluconate, 7 KCl, 2 NaCl, 1 MgCl2, 0.4 EGTA, 10 HEPES, 2 ATP-Mg, 0.3 GTP-Tris and 20 sucrose. Pipette resistance was ~6 MΩ, and the access resistance was 10-25 MΩ, which was monitored throughout the voltage-clamp recording. Resting membrane potential was 52-70 mV in current-clamp recording.

Photocurrents were first measured with pairs of 1-second long light pulses, separated by periods of darkness lasting 1 second, while holding neurons in voltage clamp at −70 mV, −30 mV and +10 mV to assay the properties of Halo. Light-induced membrane hyperpolarizations were induced by 1 second duration light pulses, separated by periods of 1 second darkness, in neurons current-clamped at resting membrane potential. Light pulse trains were synthesized by custom software written in MATLAB (Mathworks), and then played to the DG-4 light source through a digital-to-analog converter on the Digidata 1440. For the spike-blockade experiment, spikes were first induced via somatic current injection through the patch pipette. Most of the neurons patched easily fired action potentials with 100% probability, in response to ~300 pA current injections (4 ms duration). For each neuron, injected somatic current magnitudes guaranteed 100% firing rate of 20 spikes, at a rate of 5 Hz.

A DG-4 optical switch with 300-W xenon lamp (Sutter Instruments) was used to deliver all light pulses, for Halo or ChR2 activation. A Texas Red filter set (Chroma, excitation 560/55, diachronic 595LP, emission 645/75) was used to deliver yellow light to activate Halo. The same diachroic mirror was also used to deliver blue light, but with an excitation filter 480/40 in the DG-4, to allow ChR2 excitation. Note that the DC595LP dichroic mirror only reflects 35% of incident 460-500 nm light through the objective; custom-coated dichroics that reflect light all the way into the ultraviolet (as are available from companies such as Chroma) would be optimal.

According to one embodiment of the present invention, the survival replication, differentiation, or death of cells is modulated by electrical activity from Halo. With appropriate light pulses, Halo-expressing cells can be guided down any one of these pathways, depending on the precise pattern of stimulation used to drive activation of Halo. A specific electrical activity pattern results in a specific pattern of downstream signal transduction and in a specific cellular fate response. Therefore, targeting Halo to specific cells, then exposing them to particular light patterns, enables them to be optically driven towards survival, differentiation, replication, or death. This has many potential applications.

For example, in the case where the target cell is a stem cell, particular patterns of activity will drive the replication or differentiation of stem cells (including human embryonic stem cells), or drive the death of the stem cells (in the case where excessive replication is desired to cease). If the target cells are tumor or cancer cells, then targeting Halo to those cells will permit the use of specific and appropriate patterns of light to drive activity, and thus kill the tumor or cancer cells. If the target cells are immune cells, then silencing the cells can prevent the calcium waves that insure cell survival, and reduce the prevalence of autoimmune disease.

Other target cells of this kind may include secretory or organ cells or their precursors, cardiac or other muscle cells, or glial cells in the brain. In each of these cases, it is desirable to control the replication, differentiation, and death of these cells precisely. Halo will be useful for controlling these things in vitro, in vivo in experimental animals, or in vivo in humans (before or after transplantation into the body)—wherever light can be delivered, such as through the skin, via small LEDs, or lasers, or through optical fibers or thin optical endoscopes.

Screening for drugs that modulate ion channel function (e.g., blocking or facilitating ion channel function) can be accomplished using Halo to screen for drugs that modulate ion channel function. One embodiment involves one or more of the following steps:

1) stably express Halo in a cell line;
2) stably express an ion channel of interest ("channel n") in the same cell line;
3) label the cells with a voltage sensitive dye (or other indicator, see below);
4) expose said cells to light, and record the fluorescence of the voltage sensitive dye;
5) expose said cells to a candidate compound that monitors the function of channel n; and 6) expose said cells to light a second time, and record the fluorescence of the voltage sensitive dye.

If the fluorescence is greater during step 6) than step 4), then the candidate drug facilitates channel function. If the fluorescence is smaller during step 6) than step 4), then the candidate drug diminishes channel function. If the fluorescence is equal in steps 4) and 6) (allowing for any bleaching of the dye), then the drug does not affect channel function. In this way, drugs that affect channel function can be detected extremely rapidly.

Steps 1) and 2) of the above process may take several hours or days, but the resulting cell line then suffices for the screening of many (perhaps millions of) drugs, which modulate channel n. Steps 3), 4), 5), and 6) take only a few seconds each; preferably, steps 4), 5), and 6) each take less than 1 second. Steps 4), 5), and 6) take place in a robotic device that moves a 96- or 384-well plate into the focus of an optical beam (see the last section for details on devices). The wells of the plate would all contain the same cell line, in order to facilitate the screening of drugs that affect a particular channel, or each well would contain cells of a different cell line, in order to facilitate the screening of one drug against many different channels ("screening against side effects," see below).

Step 3 can include the use of a voltage-sensitive dye for fast kinetics; however, another dye (e.g., a calcium-sensitive dye in the case that channel n is a calcium channel) could also serve to indicate whether channel function is modulated by the drug. Genetically encoded indicators of voltage or calcium would also be useful for reading out the activity of the cell (e.g., FLASH, GCaMP2, cameleon, etc.). In this case, these indicators would be stably expressed in the cell line as well. Other methods of reading out whether the drug had an effect could also be useful for supplementing this readout (e.g., immunostaining for the phosphorylation of a site that is phosphorylated during or after periods of ion channel activity).

Blindness and other sensory deficits affect millions of people worldwide, severely impacting their quality of life. Halo can be targeted to somatic cells in the human patient to provide a type of sensory prostheses. For example, some forms of blindness destroy photosensor function but leave signal processing in downstream neurons intact. In such diseases, such as macular degeneration or retinitis pigmentosa, targeting Halo to the "off" retinal ganglion cells (e.g., by injecting viruses expressing Halo into the retinal cell layers inside the eye) would enable restoration of visual function. As light increases in the environment, Halo would inhibit the "off" cells, causing increased visual responses in the brain. In such patients treated with Halo targeted to retinal ganglion cells, the retinal ganglion cells would themselves become photosensitive, enabling vision with resolution comparable to the native eye, and not requiring invasive technology beyond that point. Halo is sufficiently sensitive to detect sunlight (power ~1 kW/m^2), with maximal sensitivity in the part of the spectrum that is greatest in sunlight. Expressing Halo in a retinal cell, accompanied with a projection device that would amplify the ambient light, would enable vision inside or in lowlight conditions.

Another implementation of Halo involves situations where the central nervous system neurons in a person are infected with virus expressing Halo (or otherwise come to express Halo). These neurons would then be inhibitable by pulses of yellow light. This gene therapy approach would therefore allow optical inhibition of precise neuronal targets in the brain. If the targeted neurons are epileptic, this would enable silencing of those cells without needing ablative surgery. If the targeted neurons were in the frontal cortex or other parts of the brain, these light-sensitive neurons would permit optical modulation of emotion or cognition. If the targeted neurons were in the spinal cord, neurons that mediate pain stimuli could then be inhibited by light.

In general, such a gene therapy approach opens up a new kind of generalized prosthetic in defined parts of the nervous system. The prosthetic allows light to be converted into neural activity.

In another instance, Halo is targeted to specific and different parts of a cell. For example, targeting Halo to the axon hillock using the AIS (axon initial segment) targeting sequence allows more powerful inhibition. Fusing Halo to a targeting sequence of DNA, so that the resultant protein contains both Halo and the targeting peptide, allows Halo to be sent to the presynaptic terminal, the postsynaptic terminal, the nucleus, or other intracellular compartments. Such targeting sequences include PDZ domains, glutamate and GABA receptor C-terminal sequences, ion channel C-terminal sequences, presynaptic scaffolding targeting sequences, and other targeting sequences. These versions of Halo can then be used to trigger specific intracellular signaling events, including those important for neuroprotection, memory, or other enduring signaling functions.

In a combinatorial fashion, these reagents could complement the other applications of Halo. For example, these reagents could be useful for drug screening (e.g., finding drugs that modulate the function of a channel in a particular subcellular compartment). These reagents could also be useful for prosthetic devices (e.g., driving activity on the dendrites of a neuron, to more closely mimic natural synaptic activity).

Various embodiments, including but not limited to those involving drug screening, employ an optical imaging device containing 1) a light source (LED, lamp, laser) for illuminating the cell expressing Halo and driving a change in cell voltage, 2) a light source for illuminating a dye or indicator, possibly the same light source as used for driving the voltage change, and 3) a switch for alternating between the two light sources or a beamsplitter for simultaneous non-interfering delivery of both kinds of light. The fluorescence of the dye or indicator would be measured by a sensor (CCD camera, PMT, or photodiode). This kind of device can be useful for ion channel drug screening, as described above. The device itself consists of a robotic arm for moving a plate (e.g., a 384-well plate) through the arena where the light sources and sensor are present.

In one embodiment, diagnostic applications, as mentioned herein, use a combined light source imaging device. For example, taking cells from a patient, expressing Halo in them, and then exposing them to light, can be used to reveal patient-specific ion channel syndromes in biopsy samples or in cells of the circulatory system.

For various implementations, an implantable or head-mounted LED, or other small light source can be used. Such a light source can be implanted under the skin, under the skull, deep within the brain, or deep within another organ of interest, in which Halo-expressing cells are also located (either exogenously introduced, or endogenously located and targeted with a virus). This device can be used for stimulating Halo in cells located directly adjacent to the light source. A strip of LEDs, each individually controllable, is useful. For the example of the cortical implant, a 2-dimensional array of LEDs is useful.

For medical applications, various embodiments have LEDs that are remotely powered. A remotely-powered LED can be made, for example, by combining an LED in a closedloop series circuit with an inductor. This would allow radiofrequency (RF) energy or rapidly changing magnetic fields (e.g., delivered by a transcranial magnetic resonance (TMS) coil) to temporarily power-up the inductor, and thus the connected LED, allowing local delivery of light, even deep in a brain structure. In certain embodiments, such a device is implanted under the skin, under the skull, deep within the brain, or deep within another organ of interest in which Halo-expressing cells are also located (either exogenously introduced, or endogenously located and targeted with a virus). Optionally, another device is used to remotely deliver RF or magnetic energy (e.g., placed nearby or worn on the patient) for activating the implanted device.

N. pharaonis halorhodopsin with mammalian-optimized codon usage was synthesized as a DNA sequence according to the sequence listing provided on the following page as Sequence Listing A.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For instance, such changes may include the use the use of digital logic or microprocessors to control the emitted light. Such modifications and changes do not depart from the true spirit and scope of the present invention, which is set forth in the following claims.

SEQUENCE LISTING A

The N. pharaonis halorhodpsin with mammalian-optimized codon usage was synthesized according to the following DNA sequence (876 base pairs).
ATGACTGAGACCCTCCCACCCGTGAC-
TAAAGCGCCGTCGCTCTGCAAGCAGAGGT TAC-
CCAGCOGGAGCTOTTCGAGTTCGTCCI-
CAACGACCCCCTCCTGGCTTCFAGCCT
CTACATCAACATTGCTCTGGCAGGCCTC-
TATACTGCTGTTCGTCTTCATGACCAGG GGACTC-
GATGACCCTAGGGCTAAACTGATTG-
CAGTGAGCACAKFTCTGGITCCCGTG
GTCTCTATCGCTTCCTA-
CACTGGGGGCATCTGGTCTCACAAT-
CAGTGICCTOGAA ATGCCAGCTGGCCACGC-
CGAAGGGAGCIGICATGCTGGGAGGCGAAGAGGT
CGATOGGGTTGTCACAATGTGGGGTCGC-
TACCTCACCTGGGCTCTCAGTACCCCCAT
GATCGUIGGCACTCGGACTCCMGCCG-
GAAGTAACGCCACCAAACCTTCACTGC TATTA-
CATTCGATATCGCCATGTGCGTGAC-
CGGGCTCGCAGCTGCCCTCACCACCAG
CAGCCATCTGATGAGATGGTTTTGGTAT-
GCCATCTCTTGTGCCTGCTTTGTGGTG CTG-
TATATCCTGCTGGTGGAGTGGGCICAG-
GATGCCAAGGCTGCAGGGACAGCCGA.
CATGTTTAATACACTGAAGCTGcr-
cAcrGTGGTGATGTGGCTGGGTTACCCTATCGTT
TGGGCACTCGGCGTGGAGGGAATCG-
CAGTTCTGCCTGTTGGTGTGACAAGCTGGGG
ACTCCTTCCTOGACATTGTGGCCAAG-
TATATTTTGccmcroCTOCTGAATTAT CTGACTTC-
CAATGAGTCCGTGGTGTCCGGCTCCATACTG G A
CGTGCCATCCG CCA GC GGCACACCIGCCGAT-
GACTGA).

The Halo-GFP fusion protein was generated by PCR amplification of the Halo gene with primers 5'GAATTCGC-CACCATGACTGAGACCCTCCCACCCGTG and 3'GGATCCGTCATCGGCAGGTGTGCCGCTGGC and inserted into the EcoRI and BamHI cites of pEGFP-N3 (Clontech), which has the CMV promoter. The Halo-GFP fusion protein sequence was then PCR amplified with primers 5'CCGGTGCCACCATGACTGAGACCCTC-CCACCCGTG and 3'GAATTCTTACTTGTA-CAGCTCGTCCATCGG and inserted into lentiviral vector FCK(1.3)GW containing the CaMKII promoter via AgeI and EcoRI sites. All constructs were verified by sequencing. The channelrhodopsin construct used in various experiments, FCK-hCmC, contains the human/mammalian codon-optimized gene ChR2 fused to fluorescent protein mCherry, under the CaMKII promoter.

What is claimed is:

1. An apparatus for optical stimulation of a mammalian cell expressing a light-driven chloride ion pump from *Natronobacterium pharaonis* (NpHR), the apparatus comprising:
   a stimulation source that provides a sequence of optical or electrical stimuli to the cell, each stimulus increasing the probability of a depolarization event occurring in the cell; and
   an optical source capable of providing yellow light to the cell to activate the expressed NpHR ion pump, thereby decreasing the probability of depolarization events occurring in the cell.

2. The apparatus of claim 1, wherein the stimulation source is an optical light source.

3. The apparatus of claim 1, wherein the stimulation source is an electrical pulse generator.

4. The apparatus of claim 1, wherein the optical source emits light at a wavelength of around 560 nm.

5. The apparatus of claim 1, wherein the cell also expresses a channelrhodopsin-2 ion channel and the sequence of stimuli to the cell is a sequence of optical pulses of blue light.

6. The apparatus of claim 1, further comprising a detection component for detecting changes in voltage across the cell membrane.

7. The apparatus of claim 1, wherein the cell also includes a fluorescent calcium-sensitive dye or a fluorescent voltage-sensitive dye, and the apparatus further comprises a fluorescence detector.

8. The apparatus of claim 1, wherein the stimulation source is capable of providing a sequence of optical or electrical stimuli, and the optical source capable of providing a light pulse, at a millisecond time scale.

9. The apparatus of claim 1, wherein the apparatus is configured to stimulate the cell in vitro.

10. The apparatus of claim 1, wherein the apparatus is configured to stimulate the cell in vivo.

* * * * *

SEQUENCE LISTING

<160> NUMBER OF SEQ ID NOS: 5

<210> SEQ ID NO 1
<211> LENGTH: 876
<212> TYPE: DNA
<213> ORGANISM: Artificial Sequence
<220> FEATURE:
<223> OTHER INFORMATION: mammalian codon-optimized sequence from
      Natronobacterium pharaonis

<400> SEQUENCE: 1
atgactgaga ccctcccacc cgtgactgaa agcgccgtcg ctctgcaagc agaggttacc      60
cagcgggagc tgttcgagtt cgtcctcaac gaccccctcc tggcttctag cctctacatc     120
aacattgctc tggcaggcct gtctatactg ctgttcgtct tcatgaccag gggactcgat     180
gaccctaggg ctaaactgat tgcagtgagc acaattctgg ttcccgtggt ctctatcgct     240
tcctacactg ggctggcatc tggtctcaca atcagtgtcc tggaaatgcc agctggccac     300
tttgccgaag ggagttctgt catgctggga ggcgaagagg tcgatggggt tgtcacaatg     360
tggggtcgct acctcacctg ggctctcagt accccatga tcctgctggc actcggactc     420

```
ctggccggaa gtaacgccac caaactcttc actgctatta cattcgatat cgccatgtgc    480
gtgaccgggc tcgcagctgc cctcaccacc agcagccatc tgatgagatg gttttggtat    540
gccatctctt gtgcctgctt tctggtggtg ctgtatatcc tgctggtgga gtgggctcag    600
gatgccaagg ctgcagggac agccgacatg tttaatacac tgaagctgct cactgtggtg    660
atgtggctgg gttaccctat cgtttgggca ctcggcgtgg agggaatcgc agttctgcct    720
gttggtgtga caagctgggg ctactccttc ctggacattg tggccaagta tattttgcc     780 tttctgctgc tgaattatct gacttccaat gagtccgtgg tgtccggctc catactggac    840
gtgccatccg ccagcggcac acctgccgat gactga                              876

<210> SEQ ID NO 2
<211> LENGTH: 36
<212> TYPE: DNA
<213> ORGANISM: Artificial Sequence
<220> FEATURE:
<223> OTHER INFORMATION: primer

<400> SEQUENCE: 2
gaattcgcca ccatgactga gaccctccca cccgtg                              36

<210> SEQ ID NO 3
<211> LENGTH: 30
<212> TYPE: DNA
<213> ORGANISM: Artificial Sequence
<220> FEATURE:
<223> OTHER INFORMATION: primer

<400> SEQUENCE: 3
ggatccgtca tcggcaggtg tgccgctggc                                     30

<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4
ccggtgccac catgactgag accctcccac ccgtg                               35

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
gaattcttac ttgtacagct cgtccatcgg                                     30
```